(12) United States Patent  
Hegewald et al.

(10) Patent No.: US 10,409,237 B2
(45) Date of Patent: Sep. 10, 2019

(54) METHOD AND DEVICE FOR MANAGING MOBILE DEVICES

(71) Applicant: Dräger Safety AG & Co. KGaA, Lübeck (DE)

(72) Inventors: Jan Hegewald, Düsseldorf (DE); Thielo Hammer, Düsseldorf (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 593 days.

(21) Appl. No.: 15/088,520

(22) Filed: Apr. 1, 2016

(65) Prior Publication Data

US 2016/0299479 A1    Oct. 13, 2016

(30) Foreign Application Priority Data

Apr. 7, 2015  (DE) .................. 10 2015 004 248

(51) Int. Cl.
 *G05B 15/02*  (2006.01)
 *G01N 33/00*  (2006.01)
 *G06Q 10/00*  (2012.01)

(52) U.S. Cl.
 CPC ......... *G05B 15/02* (2013.01); *G01N 33/0006* (2013.01); *G06Q 10/20* (2013.01)

(58) Field of Classification Search
 CPC ..... G05B 15/02; G01N 33/0006; G06Q 10/20
 USPC .......................................................... 700/19
 See application file for complete search history.

(56) References Cited

U.S. PATENT DOCUMENTS

| 7,723,951 | B2* | 5/2010 | Poisner .................. H02J 7/0045 320/106 |
| 2003/0131094 | A1* | 7/2003 | Awada ...................... G06F 9/468 709/224 |
| 2008/0209965 | A1* | 9/2008 | Maack .................. G06F 21/554 70/262 |
| 2010/0060410 | A1* | 3/2010 | Wirth .................... A61B 6/4405 340/5.2 |
| 2012/0007736 | A1 | 1/2012 | Worthington et al. |
| 2013/0134930 | A1* | 5/2013 | Konkle ................. H02J 7/0027 320/108 |
| 2015/0177207 | A1* | 6/2015 | Kennard ............ G01N 33/0063 73/31.05 |

(Continued)

FOREIGN PATENT DOCUMENTS

DE    10 2012 210 085 B3    3/2013
DE    10 2011 119 570 A1    5/2013

*Primary Examiner* — Robert E Fennema
*Assistant Examiner* — Christopher W Carter
(74) *Attorney, Agent, or Firm* — McGlew and Tuttle, P.C.

(57) ABSTRACT

A method and a device automatically manage mobile devices (1) with a storage device (10) with plural mobile device storage stations (12) and a mobile device maintenance station (14). A detection device (16, 18) detects the release and/or a return of a mobile device. A controller (30) is configured to determine a group of mobile devices (1) as a function of a ratio of at least one maintenance parameter of the particular mobile devices (1) to a corresponding maintenance threshold value, to select one of the mobile devices (1) from the group as a release device, to release the selected release device, and/or to receive the return device into the at least one maintenance station (14) or into one of the at least two storage stations (12) as a function of a ratio of at least one maintenance parameter of the return device to a corresponding maintenance threshold value.

2 Claims, 4 Drawing Sheets

(56) References Cited

U.S. PATENT DOCUMENTS

2017/0225889 A1* 8/2017 Edme .................. B65G 1/0457

* cited by examiner

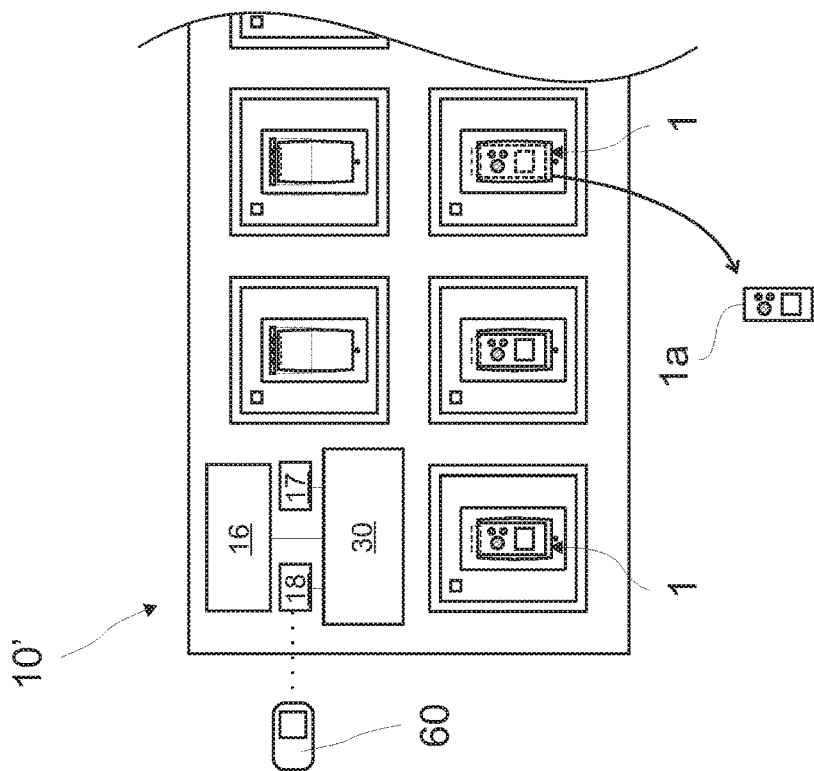
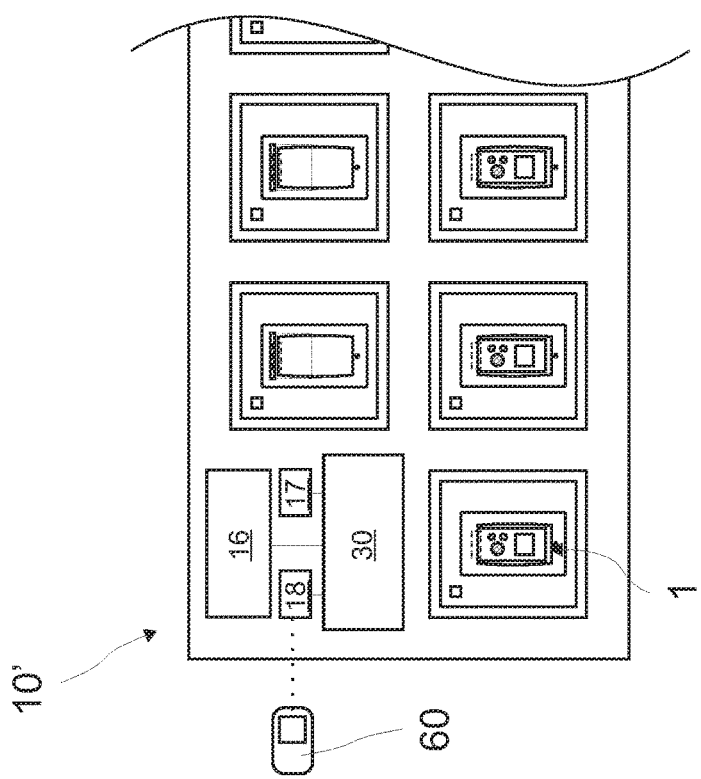

METHOD AND DEVICE FOR MANAGING MOBILE DEVICES

CROSS REFERENCE TO RELATED APPLICATIONS

This application claims the benefit of priority under 35 U.S.C. § 119 of German Patent Application 10 2015 004248.3 filed Apr. 7, 2015, the entire contents of which are incorporated herein by reference.

FIELD OF THE INVENTION

The present invention pertains to an automatic method and a device for managing mobile devices.

BACKGROUND OF THE INVENTION

Mobile devices such as gas-measuring devices, especially portable gas-measuring devices, are used, in industrial plants, business premises and public buildings, wherever humans and property have to be protected against injuries and damage. The gas concentration of at least one gaseous substance can thus be monitored in a large industrial plant such as a refinery. The gas concentrations to be monitored concern, for example, the lower explosion limit or threshold values of gases, for example, carbon monoxide, hydrogen sulfide, oxygen, or other toxic gas substances. Lower explosion limit is defined as the limit that leads to explosion when coming into contact with an external energy source, for example, a spark. A toxic gaseous substance is generally designated as a gaseous or vaporous hazardous material which has specific hazardous properties or other chronically damaging properties. Gas-measuring devices known in the state of the art generally possess one or more gas inlet openings, through which the gaseous substance to be tested is fed to corresponding sensors in order to measure the gas concentration of the corresponding gaseous substances. An optical and/or acoustic alarm is triggered if it is detected in a gas-measuring device that the concentration of a toxic substance of the gas being tested exceeds a defined threshold value. To guarantee a reliable operation of such gas-measuring devices, a maintenance, i.e., to test, to adjust and/or to calibrate them, is required at regular intervals. A test is essentially defined as a simple test of operation of a gas-measuring device. Regular settings are made during an adjustment in order to check and to set the zero point and the sensitivity of the gas-measuring device with a known zero gas or test gas without parameters, e.g., gas species, measuring range, alarm thresholds and special applications set during the initial startup being changed. During a calibration, the display of the gas-measuring device is compared with a known test gas concentration.

For testing, adjusting and/or calibrating gas-measuring devices, a test station is known, for example, from DE 10 2012 210 085 B3 for a portable gas-measuring device for at least one test gas with a device for receiving the gas-measuring device, a test gas supply, a pivotable flap for covering at least one area with gas inlet openings of the exposed surface of a gas-measuring device received in the receiving area and with a seal. A method for operating a gas concentration monitoring system for detecting the gas concentration of at least one gaseous substance is known from DE 10 2011 119 570 A1.

Further, interconnecting a plurality of such test stations in a storage device in order to make possible the maintenance of a plurality of gas-measuring devices at the same time is known in the state of the art. However, a disadvantage of such storage devices is that the individual maintenance stations are very expensive and thus lead to considerable costs for such storage devices. In addition, in storage devices available in the state of the art, which consist, for example, of a plurality of docking stations for gas-measuring devices, there is the risk that non-maintained gas-measuring devices will also be released to the user, because they can be simply removed from the docking station. It is also known to display the maintenance status of a gas-measuring device via a lamp; however, this does not hinder the untrained user from removing a gas-measuring device which is displayed as not maintained by a lamp flashing red, for example. In particular, the user could inadvertently interpret the lamp flashing red, for example, as an indication of a charging state and not for a maintenance status such as a calibration status of the gas-measuring devices.

SUMMARY OF THE INVENTION

An object of the present invention is therefore to at least partly avoid the disadvantages described above in a method and a device for managing mobile devices, especially gas-measuring devices. In particular, an object of the present invention is to provide a method and a device for the automated storage, release and/or receipt of mobile devices.

In this case, features and details which are described in connection with the method apply, of course, also in connection with the device according to the present invention and vice versa, so that reference is or can always be made mutually in relation to the disclosure of the individual aspects of the present invention.

According to a first aspect of the present invention an automatic method for managing mobile devices in a storage device with at least two storage stations, at least one maintenance station, at least one controller and at least one detection device is provided, having the following steps:
  Detection of a desire (intention/request/wish) to release for the release of one of the mobile devices from the storage device by means of the detection device,
  determination of a group of mobile devices as a function of a ratio of at least one maintenance parameter of the particular mobile devices to a corresponding maintenance threshold value by means of the controller,
  selection of one of the mobile devices from the group as a release device by means of the controller, and
  release of the selected release device by means of the controller.

Mobile devices can be fully automatically and autonomously managed with this method. Such mobile devices can, in particular, be automatically stored and automatically released in a specific manner.

According to the present invention, the storage device has at least two storage stations and at least one maintenance station. The storage stations are each configured for storing a mobile device. Thus, each storage station may have, for example, an area for receiving a mobile device. The maintenance stations are used for maintaining mobile devices. The maintenance stations may each receive a mobile device for this. They may therefore likewise have an area for receiving a mobile device. In addition, each maintenance station is configured for maintaining mobile devices. This does not apply to the storage stations. Thus, a maintenance station is distinguished from a storage station by additional maintenance interfaces and/or means to or for a mobile device. A mobile device can first be maintained by means of the maintenance station according to the present invention.

The corresponding device can, in particular, be tested, adjusted and/or calibrated. In particular, a charging of a battery or a corresponding storage devices may not be defined as maintenance or not as maintenance means in the sense of the present invention.

The storage device according to the present invention may be configured, for example, as a storage cabinet with a plurality of storage compartments. The at least two storage stations may each be formed by one of the storage compartments. Another of the storage compartments may be used for the at least one maintenance station. In this case, maintenance means and/or interfaces are provided in the corresponding storage compartment for a maintenance station to make possible the maintenance of a mobile device. The maintenance interfaces are used and/or configured for communication with a controller and/or for the exchange of fluids between the corresponding mobile device to be maintained and a fluid source.

In another embodiment, a storage station or a maintenance station may each be provided in the storage compartments. However, the storage device may also be configured without a storage cabinet from a combination of the at least two storage stations and the at least one maintenance station. In this case, the at least two storage stations and the at least one maintenance station are preferably configured as docking stations.

In case of mobile devices having a battery, the storage stations and/or the at least one maintenance station may each have and/or form a storage device. Thus, they may each also be used for charging a battery. The storage device in this case is not used for maintaining the mobile devices. Further, it is possible in the sense of the present invention that the storage stations and/or the at least one maintenance station are each configured as a storage compartment or as a storage chamber, in which a mobile device or a plurality of mobile devices can be inserted and stored.

Detection of a desire to release for the release of the mobile device by means of the detection device is defined by the entry of a desire to release of a user, for example, into a command acceptance unit such as a touchscreen or a user interface provided with physical keys being detected.

Moreover, the determination of a group of mobile devices is provided by means of a controller. The group according to the present invention is not limited to a plurality of mobile devices, but may also have only a single mobile device. Thus, a specific group may have, for example, several tens or hundreds of mobile devices or only a single mobile device.

The determination of the group of mobile devices by means of the controller is used for classifying the mobile devices. Thus, the mobile devices of the specific group of mobile devices may have the common property that they each meet a required and preassigned state of maintenance. Such a group is determined by means of the maintenance parameter of the mobile devices. If the maintenance parameter of a particular mobile device is set to a ratio to a corresponding maintenance threshold value, it can be determined on the basis of the ratio whether or not the particular device belongs to the group according to the present invention. The particular mobile device belongs to the group when the corresponding ratio corresponds, for example, to the fact that the particular device has at least a required state of maintenance. Otherwise, the particular mobile device does not belong to the group because it does not have—in relation to the previous case—the required state of maintenance.

A maintenance parameter, i.e., a detected or determined maintenance parameter, is, for example, a charging state of a battery of a mobile device. Another example of a maintenance parameter is, for example, a calibration state of a mobile device, especially when this is configured as a gas-measuring device. As an alternative or in addition, a maintenance parameter may correspond to a state of operation of a mobile device, in particular, of a corresponding component. Thus, the maintenance parameter may correspond, for example, to the state of operation of a display of a mobile device. If a display damage occurs in this case, the maintenance parameter changes. This is especially meaningful in case of a gas-measuring device as a mobile device because the user would otherwise discover only too late the display damage in an unfavorable case. A maintenance threshold value is, for example, a preassigned maintenance threshold value or an assignable maintenance threshold value.

In the selection of one of the mobile devices from the group, a mobile device can be selected, for example, on the basis of a priority or via a random generator from a selection list. It is, for example, thus possible that in the specific group, a priority among the mobile devices of the group is assigned on the basis of various ratios of particular maintenance parameters to corresponding maintenance threshold values, and a specific position in a correspondingly prepared selection list, for example, the first position, is always selected. When the specific group has, for example, 100 mobile devices, each with a specific charging state of the battery or different charging states of the particular batteries of the mobile devices, the mobile device with the lowest or highest charging state may always be selected.

A release of a mobile device by means of the controller is especially defined as the release, i.e., the mechanical and/or electronic unlocking of a storage station or a maintenance station for the removal of the mobile device by a user. I.e., in case of a release, a user is able to remove the selected mobile device from the storage device without aid or overcoming obstacles. According to the present invention, it is thus not necessary for the selected mobile device to be moved in case of the release. Thus, the release of the selected release device may, for example, be that a mechanical unlocking is triggered, by means of which the release device can be uncoupled from the storage device and is thus mechanically released. The release device may also be released, not only in the storage station or maintenance station in case of a release, but may be moved by means of a transport device, for example, fully automatically, to the user or at least within the reach of the user.

According to a preferred variant of the present invention, the at least one maintenance parameter may characterize a particular state of operation of the mobile devices and the maintenance threshold value corresponding to the particular maintenance parameter may correspond with an operability of the particular mobile devices. It can consequently be ensured that only operable mobile devices will be released to a user. A state of operation may be defined as the mechanical and/or electronic state of an operation of a mobile device or the mechanical and/or electronic property of the mobile device. Thus, a high maintenance parameter may indicate, for example, an operation of the mobile device that is fully present and/or available for use. By contrast, a low maintenance parameter indicates a limited operation of the mobile device. The maintenance threshold value is preferably intended to be able to form a criterion of decision, for example, between an operation still sufficient for a desired use and an operation no longer sufficient for use. The maintenance threshold value is thus used for categorizing the actual state of operation of the mobile device. The maintenance threshold value thus characterizes, for example, a minimal state of the operation that a mobile device should have. Hence, the operability indicates whether or not the mobile device is operating. I.e., the mobile device is not determined to be a mobile device of the group when the maintenance threshold value indicates, for example, that a mobile device is actually not operating, and the maintenance threshold value indicates a value for an operation of the mobile device because the ratio of the actual maintenance parameter to the maintenance threshold value is taken into consideration in the determination of the group.

In addition, according to the present invention the at least one maintenance parameter may characterize a particular remaining running time of the mobile devices and the corresponding maintenance threshold value corresponds with a minimally required remaining running time of the particular mobile devices. Because of the analogous design, reference is analogously made to the explanations, advantages and preferred features of the preceding paragraph. Because of the characterization of the remaining running time by the maintenance parameter, a user receives only mobile devices, the particular remaining running time of which corresponds to a minimally required remaining running time because only those devices, the remaining running time of which is greater than the minimally required remaining running time, are selected in the determination of the group of mobile devices. When the mobile devices are gas-measuring devices and the minimally required remaining running time corresponds with a calibration state of the gas-measuring devices, for example, only calibrated gas-measuring devices, i.e., gas-measuring devices, which, in relation to their calibration state, still have a remaining running time that is longer than the minimally required remaining running time, can be released to the user. The present invention is not, however, limited to the fact that the minimal remaining running time corresponds with a calibration state. Thus, it is also possible that the minimal remaining running time corresponds with a charging state, an operation testing time, a use-by date and/or the like. Thus, in preferred variants, for example, only mobile devices with a specific minimal charging state of the battery of same, a specific, mostly elapsed operation testing time and/or a not yet reached use-by date can be released. It can consequently be guaranteed that the user only receives mobile devices, with which he can or may still work for a specific time. According to this variant, it is, further possible that only operable devices with a specific minimal remaining running time can be released to the user. The minimally required remaining running time may be in the range of hours, days, weeks or months. It is preferably within a day in case of gas-measuring devices. The minimally required remaining running time depends, in particular, on an assumption for how long the user will presumably use the mobile device or when and for how long the mobile device will be used as of the release from the storage device.

Further, it may be advantageous according to the present invention when the mobile device that has the shortest remaining running time is selected by the controller to be a release device. Thus, it can be achieved that mobile devices with an as current as possible state of maintenance are always in the storage device, and assuming a correspondingly high lending rate or release rate, none of the mobile devices has a maintenance parameter which no longer has the minimally required remaining running time. It is especially advantageously possible to create an autonomous storage device—assuming the required release rate—by this method according to the present invention.

In addition, it is possible according to the present invention that the release device is selected from the at least one maintenance station, when the at least one maintenance station is occupied by a mobile device of the group. It can consequently be achieved that whenever possible a maintenance station is free for receiving a mobile device to be maintained. I.e., in case of a plurality of maintenance stations which are all occupied, when selecting a release device, it is preferred to select one from the maintenance stations. In case of a plurality of maintenance stations, which are only partly occupied with mobile devices, it is preferred to release release devices from the maintenance stations until all maintenance stations are free. As an alternative, it is, however, also possible to release release devices from particular storage stations even though there are still mobile devices in some of the maintenance stations. An occupied storage station or maintenance station is here a storage station or maintenance station with a mobile device received in it. A free storage station or maintenance station is a storage station or maintenance station without a mobile device received in it.

In addition, it is advantageous according to the present invention when a warning signal is sent out when it is detected that the ratio of the at least one maintenance parameter of one of the mobile devices to the corresponding maintenance threshold value does not correspond to a desired ratio. This has the advantage that in case of a too low frequency of releases and returns, for example, a technician may be informed, who replaces mobile devices which are too old or which have not been maintained in due time or places them from a storage station into a maintenance station. The warning signal in this connection may be sent acoustically, optically or in the form of an electronic message. The signal may preferably be sent in the form of a message with corresponding instructions or status information about the mobile device in question. The desired ratio may correspond, for example, with the minimally required remaining running time or with a time, over which the mobile device may be received in a storage station without maintenance. When the mobile device is, for example, a gas-measuring device, a maintenance parameter of the gas-measuring device is "121 days since the last calibration" and the maintenance threshold value presumes "at most 120 days since the last calibration," the gas-measuring device would no longer be calibrated by one day and a "120/121" ratio would no longer correspond to the desired ratio, which presumes, for example, a result ">1" in relation to days. In this case, a warning signal would be sent out after 121 days without calibration of the gas-measuring device.

According to a preferred variant of the present invention, the release device is released as a function of a lending rate of a user. Thus, it can be set, for example, that only one mobile device per day may be released to a specific user. It can, for example, be prevented by mobile devices being released as often as desired to users who do not handle the lent devices with sufficient caution or who tend to misplace released mobile devices.

According to another aspect of the present invention, an automatic method is further provided for managing mobile devices in a storage device with at least two storage stations, at least one maintenance station, at least one controller and at least one detection device, having the following steps:

Detection of a desire to return for the return of a mobile device as a return device by means of the detection device, and receiving of the return device either into the at least one maintenance station or into one of the at least two storage stations as a function of a ratio of at least one maintenance parameter of the return device to a corresponding maintenance threshold value by means of the controller.

Mobile devices can be fully automatically and autonomously managed or received and stored in a specific manner with this method.

Receiving in the sense of the present invention is defined, for example, as receiving the return device into a storage station or a maintenance station of the storage device, which is released by a user for opening and/or inserting a mobile device. This receiving is executed by a controller, which actuates a corresponding release mechanism. I.e., receiving in the present case is defined, in particular, as a release of a storage station or of a maintenance station for making possible a return or of an insertion of the return device into the storage station or the maintenance station.

The desire to return can be detected by means of a detection device, for example, by means of a barcode scanner, QR code scanner or RFID scanner. The desire to return may also be detected via a touchscreen or the like to be actuated by the user.

In relation to the maintenance parameter as well as the maintenance threshold, the method explained above applies.

According to a variant of the present invention, the at least one maintenance parameter characterizes a state of operation of the return device and the corresponding maintenance threshold value corresponds with an operability of the return device. The return device can advantageously consequently be received into the at least one maintenance station or into one of the storage stations. When it is detected, for example, during the receipt of the return device, that this device is no longer operating, i.e., that the state of operation of the return device does not correspond to the required maintenance threshold value or falls below same, it can, in particular, be avoided that this no longer operating return device is received into a maintenance station, in which it could not be repaired, but only occupies a valuable storage space compared to the storage station.

Further, it is possible that the at least one maintenance threshold characterizes a remaining running time of the return device and the corresponding maintenance threshold value corresponds with a minimally required remaining running time of the return device. Consequently, in case of falling below the minimally required remaining running time, the return device can, for example, preferably be received into a maintenance station, in which the return device can be maintained. If the return device has, by contrast, a sufficient remaining running time, it may preferably be received into a storage station and the maintenance station is kept free for a return device which is possibly arriving later and is to be maintained. An efficient and resources-saving method for managing mobile devices can consequently be achieved.

In addition, it is possible according to the present invention that in a case, in which at least one maintenance station is free, the return device is received into a storage station, when the return device is not one of a number of mobile devices with the shortest remaining running times and the number of mobile devices with the shortest remaining running times corresponds to the number of the at least one free maintenance station. It can consequently be ensured that the at least one maintenance station is always kept free for the number of mobile devices with the shortest remaining running times. When the return device is, for example, a first gas-measuring device and the remaining running time corresponds with a calibration state or calibration time, the first gas-measuring device is received into a storage station when it is detected that, for example, only two maintenance stations are still free and a second and a third gas-measuring device each with a shorter remaining running time than the first gas-measuring device are still being used, i.e., are not in the storage device. The particular remaining running times of the mobile devices can consequently always be kept as current or long as possible.

In addition, it is possible according to the present invention that a warning signal is sent out when it is detected that the ratio of the at least one maintenance parameter of the return device to the corresponding maintenance threshold value does not correspond to a desired ratio. It can consequently be prevented that, for example, return devices that are no longer operating as well as return devices, which cannot be maintained in the at least one maintenance device, are received into the storage device and block, for example, a storage station there. In relation to the alarm and the desired ratio, the statements made above in this regard apply in an analogous manner.

In a preferred variant of the present invention, it is possible that, when it is detected that a ratio of the at least one maintenance parameter of at least one mobile device in a maintenance station to a corresponding maintenance threshold value does not correspond to a desired ratio, users are requested during the return of the return device to remove the at least one mobile device from the maintenance station and place it in a storage station. Consequently, the method according to the present invention can be used by a user who would like to receive a mobile device or to use it from the storage device to execute a managing action in the storage device. Thus, it is not or it is at least rarely necessary to provide management personnel as such for the storage device. The request according to the present invention may take place, for example, by means of a corresponding connection of the storage device or of the storage stations and/or of the at least one maintenance station. Thus, it is, for example, possible that in this case at first the corresponding maintenance station is released and the user, who would like to borrow a mobile device, for example, via a touchscreen, is requested to remove the device in question from the corresponding maintenance station. A selected storage station can subsequently be released and the user can be further requested to place the mobile device in question into this storage station. The actual release process is started or can be executed for the user only after the device in question has been placed into this storage station and this storage station has been locked for removal again.

According to another aspect of the present invention, a device for managing mobile devices is provided, having a storage device with at least two storage stations for storing one of the mobile devices and at least one maintenance station for storing and maintaining one of the mobile devices. A detection device is provided for detecting a desire to release for the release of one of the mobile devices from the storage device. A controller is provided for executing the above-described method. The controller is configured to determine a group of mobile devices as a function of a ratio of at least one maintenance parameter of the particular mobile devices to a corresponding maintenance threshold value, to select one of the mobile devices from the group as a release device, and to release the selected release devices.

According to another aspect of the present invention, a device for managing mobile devices is provided, having a storage device with at least two storage stations for storing one of the mobile devices and at least one maintenance station for storing and maintaining one of the mobile devices, a detection device for detecting a desire to return for the return of a mobile device as a return device, and a controller for executing the above-described method, the controller being configured to receive the return device into the at least one maintenance station or into one of the at least two storage stations as a function of a ratio of at least one maintenance parameter of the return device to a corresponding maintenance threshold value.

Mobile devices, for example, gas-measuring devices, can be managed in an automated manner at any location by means of such devices. In particular, they can be received, stored and/or released.

The controller is preferably configured as a central control and/or regulating unit and may be part of a computer unit. The detection device may be provided as a user interface, for example, as a touchscreen and/or an input device to be operated with physical keys, as a result of which the user desire can be inputted via finger input on the touchscreen or via the keys and thereby detected. The input device may, as an alternative or in addition, be configured as a barcode scanner, QR code scanner and/or RFID scanner. A touchscreen is preferably provided for detecting the desire to release and a barcode scanner, QR code scanner and/or RFID scanner is preferably provided for detecting the desire to return. The releasing and receiving of the mobile devices preferably function in conjunction with a mechanical and/or electronic locking device, which mechanically releases or locks the selected release device or return device for releasing and removal or return for a user.

In case of the releasing and/or receiving according to the present invention, a transport device may additionally be provided. This transport device is preferably automated. The transport device may be configured to transport the release device from a storage device or a maintenance station to a user or at least within his reach and/or to transport the return device from the user into a selected storage station or maintenance station.

According to a variant of the present invention, a warning signal release device may, furthermore, be provided, which is configured such that it sends out a warning signal when it is detected that the ratio of the at least one maintenance parameter of one of the mobile devices in a storage station or a maintenance station to the corresponding maintenance threshold value does not correspond to a desired ratio, or when it is detected that the ratio of the at least one maintenance parameter of the return device to the corresponding maintenance threshold value does not correspond to a desired ratio. The warning signal release device may be configured for sending an optical, acoustic and/or electronic warning signal. In a case, in which the maintenance status of at least one of the mobile devices does not correspond to the desired ratio, for example, a technician may consequently be informed about this status and a corresponding warning signal may be sent to the storage station and/or maintenance station. Further, the same advantages, as they were already explained concerning the above method in relation to the warning signal release, are obtained in this variant.

In addition, it is possible that the at least two storage stations and the at least one maintenance station are each configured as docking stations. They may each have a mechanical locking device for one of the mobile devices. Thus, a release device can be mechanically unlocked in case of a release and/or a return device can be mechanically locked after receiving. An especially cost-effective and compact storage device can consequently be provided. Compared with a storage cabinet, in which the at least two storage stations and the at least one maintenance station are provided, for example, in their own lock boxes, it is sufficient according to this variant to provide the docking stations with the necessary release mechanism for the mechanical receiving and releasing of the mobile devices. A docking station is at least essentially a receiving device, by means of which the mobile devices can be connected to a fixed network, for example, to a power grid and/or to a gas grid. The mechanical locking device may be provided, for example, in the form of a claw-like snap-in device. Thus, the locking device can at least partly enclose the mobile device, for example, the gas-measuring device, after an insertion into the storage station or the maintenance station and thus lock the mobile device for the removal by a user. The mechanical locking device ensures that only mobile devices are released from the specific group to the users and these users do not inadvertently remove a non-maintained and/or non-operating mobile device from a docking station.

In addition, it may be advantageous according to the present invention when the storage device is configured as a storage cabinet and the at least two storage stations and the at least one maintenance station are each provided in a closable storage compartment, which can be mechanically unlocked in case of a release of a release device and/or in case of a receipt of a return device. A storage device that is particularly safe for the mobile devices can consequently be provided. The mobile devices can be well protected against environmental effects in the storage compartments of the storage cabinet. The storage cabinet and the storage compartments are not limited to a specific size or shape. The number of storage compartments is as desired and may be varied depending on area of application. It can be ensured by means of the closable, i.e., lockable or sealable, storage compartments, that only maintained mobile devices or mobile devices of the specific group are released to the users and these users do not inadvertently remove a, for example, non-maintained mobile device from a docking station. Further, an additional mechanical locking device is possible in the storage stations or the at least one maintenance station in the closable storage compartments.

In an advantageous variant of the present invention, the ratio of the number of the at least one maintenance station to storage stations is less than or equal to 1:2. In this connection, the ratio of the at least one maintenance station to the storage stations is, in particular, provided as a function of an expected day use, i.e., of an expected frequency of releases and receipts of the mobile devices and a prescribed maintenance interval. A single maintenance station or calibration station would be sufficient to calibrate each gas-measuring device within the calibration interval of 120 days and thus to automatically always obtain a valid calibration of the particular gas-measuring devices in 120 storage stations and in 240 borrowings, i.e., 240 releases and 240 receipts, in case of gas-measuring devices as mobile devices and a calibration interval of, for example, 120 days. If 12 maintenance stations were now provided in 120 storage stations, i.e., if the ratio were 1:10 and thus less than 1:2, each gas-measuring device would be calibrated within the calibration interval of 120 days in case of a number of 1920 borrowings in 120 days, which are still below a number of borrowings that is usual in practice for such a case, wherein the oldest calibration would only be 10 days old. An optionally necessary operation test could thus further be fulfilled, which is necessary in case of gas-measuring devices, for example, every 10 days. The ratio of the at least one maintenance station to the storage stations in this case depends heavily on the area of application of the device according to the present invention. In highly contaminated areas, in which a frequent exchange of mobile devices is expected, the ratio should be selected to be correspondingly higher, for example, 1:4 to 1:2. The ratio is not limited to 1:2 here, but rather may also be increased to markedly above 1:2 in case of corresponding ambient conditions and lending rates.

In any case, it is possible due to the device according to the present invention and the corresponding method to manage a plurality of mobile devices such as gas-measuring devices with only a small number of maintenance stations and consequently to guarantee a maintained and calibrated state of the mobile devices or gas-measuring devices. Thus, considerable costs can be saved compared to a system which consists exclusively of maintenance stations.

It is additionally advantageous when the storage device has a number of mobile devices, which corresponds to the number of storage stations. I.e., in a storage device fully equipped with mobile devices, all storage stations are occupied by mobile devices and the at least one maintenance station is empty. An automated and, in principle, autonomous run can be ensured by means of the at least one maintenance station as buffer storage. For example, an autonomous releasing, storage and receiving of the mobile devices can thus take place.

Further measures improving the present invention appear from the following description of various exemplary embodiments of the present invention, which are schematically shown in the figures. All features and/or advantages coming from the claims, description and drawings, including structural details and spatial arrangements, may be essential to the present invention both in themselves and in various combinations.

The present invention is described in detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 3a is a schematic view of state of a method according to the present invention for managing mobile devices;

FIG. 3b is a schematic view of another state of the method according to the present invention for managing mobile devices;

DESCRIPTION OF THE PREFERRED EMBODIMENTS

Figure 1:
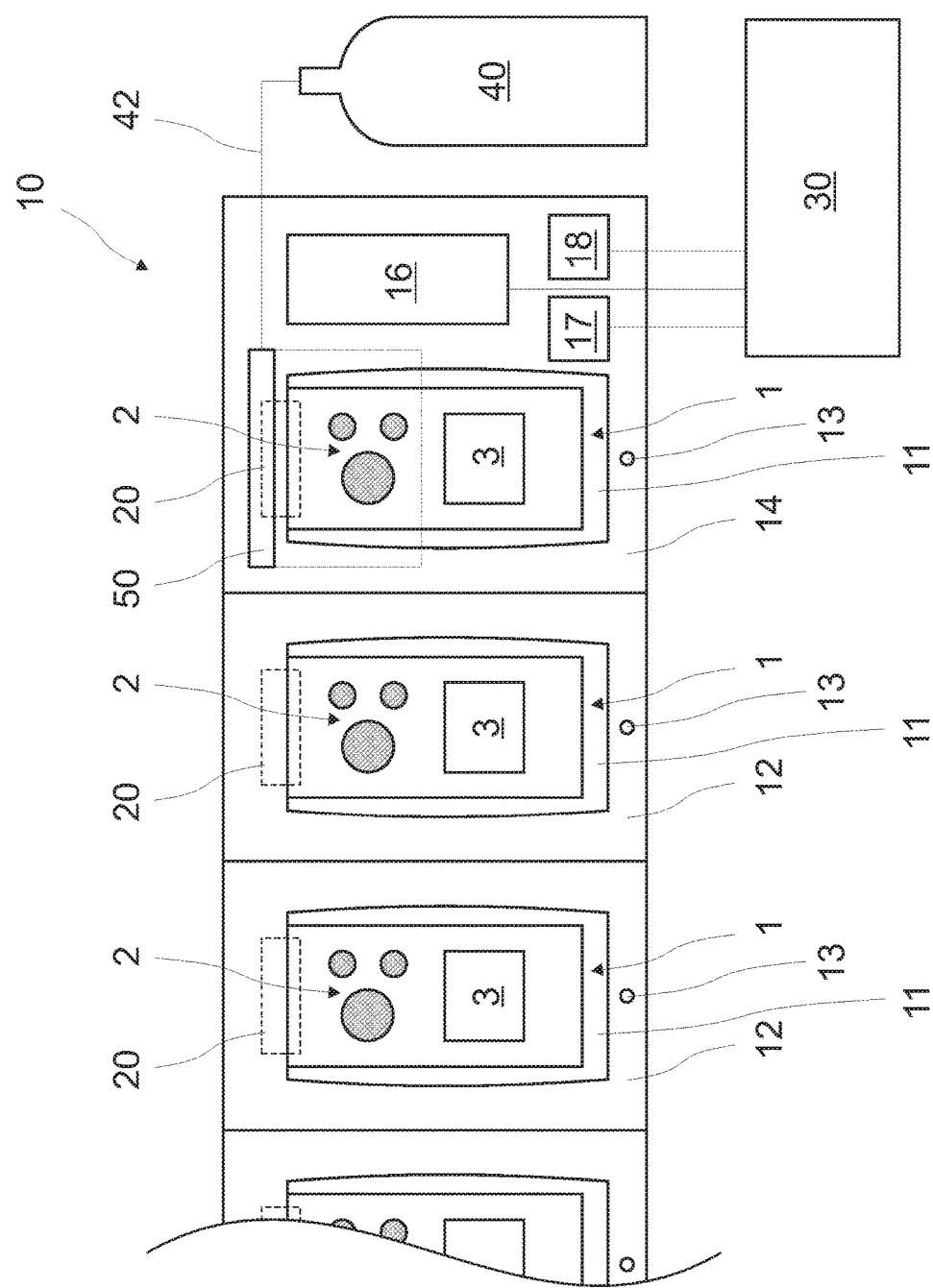
FIG. 1 is a schematic view of a device according to the present invention for managing mobile devices according to a first embodiment.

Referring to the drawings, components having identical function and mode of action are each provided with identical reference numbers in FIGS. 1 through 3d.

FIG. 1 schematically shows a device according to the present invention for automatically managing mobile devices and more specifically gas-measuring devices 1 according to a first embodiment of the present invention. The device for automatically managing gas-measuring devices 1 shown in FIG. 1 is provided as a storage device 10 with a plurality of interconnected storage stations 12 and a maintenance station 14, which is configured as a calibrating station. The storage stations 12 and the maintenance station 14 are configured as docking stations.

Besides the maintenance station 14, there is a detection device 16, 18 or a release-desire detection device in the form of a user interface, for example, a touchscreen for detecting a desire to release for the release of the gas-measuring device 1. The release-desire detection device 16, 18 in this case does not have to be provided as an integrated component of the storage device 10, but rather may also be provided as an external device, which, for example, is connected to the device for managing gas-measuring devices 1 only via a cable or in a wireless manner, for example, via a wireless connection. In the storage device 10 shown in FIG. 1, a gas-measuring device 1 is received in each storage compartment 11 in the storage stations 12 and the maintenance station 14. Each of the gas-measuring devices 1 has a touchscreen 3 as well as gas inlet openings 2 for receiving various gaseous substances. The gas-measuring devices 1 can be locked and unlocked by means of a mechanical locking device 20 in the docking stations each by means of a controller 30 of the device for managing gas-measuring devices 1. The gas-measuring devices 1 may be mechanically released and unlocked or locked by means of the mechanical locking device 20 for removal by a user selectively or as a function of specific control parameters, for example, a calibration state of the gas-measuring devices 1.

A gas feed line 42, via which a test gas can be fed from a gas source 40 to the maintenance station 14, is further integrated into the device for managing gas-measuring devices 1 shown in FIG. 1. A flap 50, which is pivotable about the free area of the gas inlet openings 2 of the measuring device 1, is provided for this. A lamp 13 is used for the optical display of a state of the particular gas-measuring device 1, which has been released or locked by means of the mechanical locking device 20. This has the advantageous effect that a user does not have to first try to remove the gas-measuring device 1 from a docking station, but rather it is directly displayed whether it is released for removal or locked.

The detection device 16, 18 has, further, a return-wish detection device in the form of a barcode scanner, QR code scanner or RFID scanner. The return-wish detection device, like the release-desire detection device, does not have to be provided as an integral component of the storage device 10, but rather may also be provided as a separate component.

The device for managing gas-measuring devices 1 shown in FIG. 1 has, further, a warning signal release device 17. The warning signal release device can be connected, for example, to the lamp 13, which lights up in a specific color in case of an error.

Figure 2:
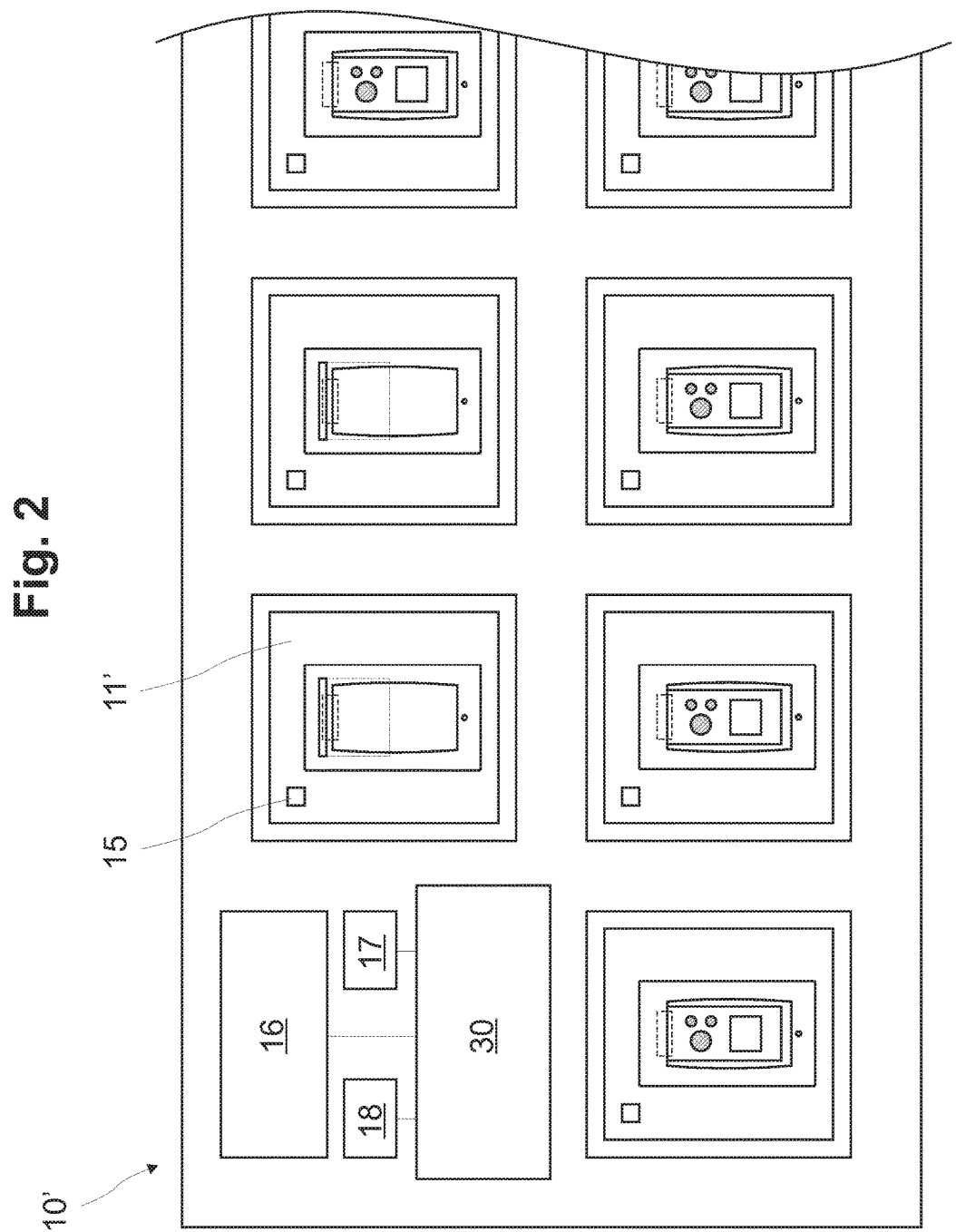
FIG. 2 is a schematic view of a device according to the present invention for managing mobile devices according to a second embodiment.

FIG. 2 shows a device for automatically managing gas-measuring devices 1 according to a second embodiment of the present invention. For simplified viewing and for avoiding a figure overloaded with reference numbers, a repetition of the reference numbers already shown in FIG. 1 was partly omitted in FIG. 2. The second embodiment shown in FIG. 2 differs, in particular, from the first embodiment shown in FIG. 1 by the storage device 10' being provided as a storage cabinet and storage stations 12 and maintenance stations 14 being stored in storage compartments 11', which are configured as sealable or lockable cabinet compartments. The storage compartments 11' shown in FIG. 2 have, further, each a door handle 15 for the facilitated opening and closing of storage compartment doors after the mechanical locking device 20 has been unlocked by a corresponding instruction from the controller 30. Even though the mechanical locking device 20 in FIG. 2 is only shown in the docking stations, it may, in addition or preferably as an alternative, also be provided in the storage compartments 11' as a locking means (locking device) for the storage compartment doors. The mechanical locking means 20 is, however, not limited thereto. Rather, the locking means may be any locking device insofar as such locking device can prevent a user from removing a gas-measuring device 1 from a storage compartment 11' or from a storage station 12 or from a maintenance station 14.

FIGS. 3a through 3d show a method for managing mobile devices or gas-measuring devices 1 in a storage device 10' with a plurality of storage stations 12 and a plurality of maintenance stations 14. For a simplified viewing of the method according to the present invention, the reference numbers shown in FIGS. 1 and 2 are partly omitted in FIGS. 3a through 3d.

According to the view in FIG. 3a, a user comes, for example, with an ID card 60 to the storage device 10' to borrow a gas-measuring device 1. Two empty maintenance stations 14 are provided in the storage device 10' shown in FIG. 3a. The detection device 16, 18 is configured, for example, as a touchscreen. In this case, a correspondingly shown button can be actuated on a start screen of the touchscreen during the release process and the desire to release can be communicated for detection. After a selection has been made, it is, further, possible that the user ID is scanned in order to assign the gas-measuring device 1 to be released to a specific user and/or to check an authorization of the user. This may also take place before the actuation of the touchscreen.

After the desire to release of the user for the release of the gas-measuring device 1 has been detected, a group of gas-measuring devices is determined as a function of a ratio of at least one maintenance parameter, for example, of a calibration time or state of the particular gas-measuring devices to a corresponding maintenance threshold value or calibration threshold value. The calibration states may either be recorded beforehand in case of new gas-measuring devices 1 or be detected by means of the detection device 16, 18 and recorded in the system in case of old, i.e., already used or borrowed gas-measuring devices 1.

As shown in FIG. 3b, one of the gas-measuring devices 1 is now selected from the specific group as a release device 1a and released, i.e., released for removal by the user. This occurs, for example, by unlocking the storage compartment 11'. The release device 1a shown in FIG. 3b is an operating gas-measuring device with a minimally required remaining running time, and preferably the shortest remaining running time. Because the two maintenance stations 14 shown in FIG. 3b are free, a gas-measuring device 1 is selected from a storage station 12. For example, a storage compartment door of the storage compartment 11' can be opened with the release device 1a for this.

Figure 3D:
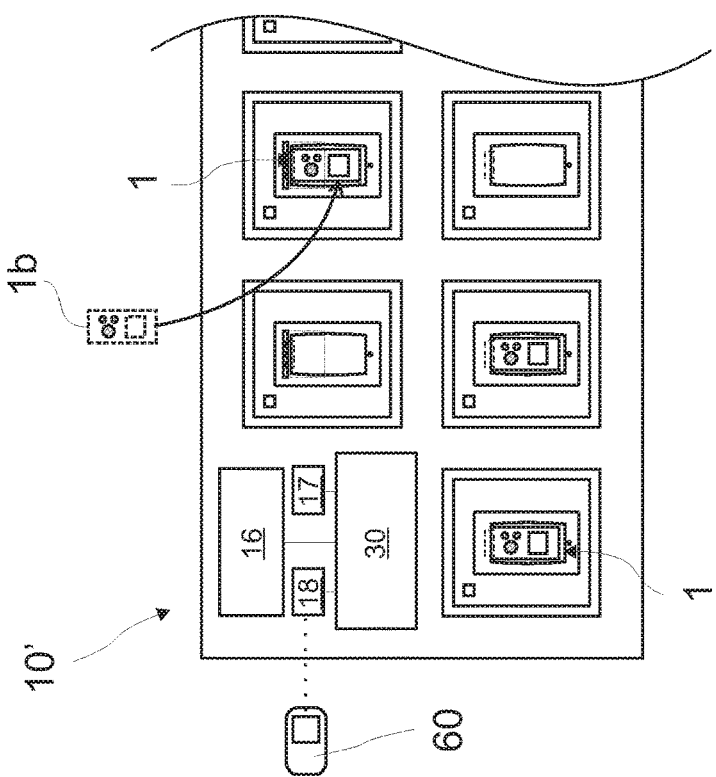
FIG. 3d is a schematic view of another state of the method according to the present invention for managing mobile devices.
Figure 3C:
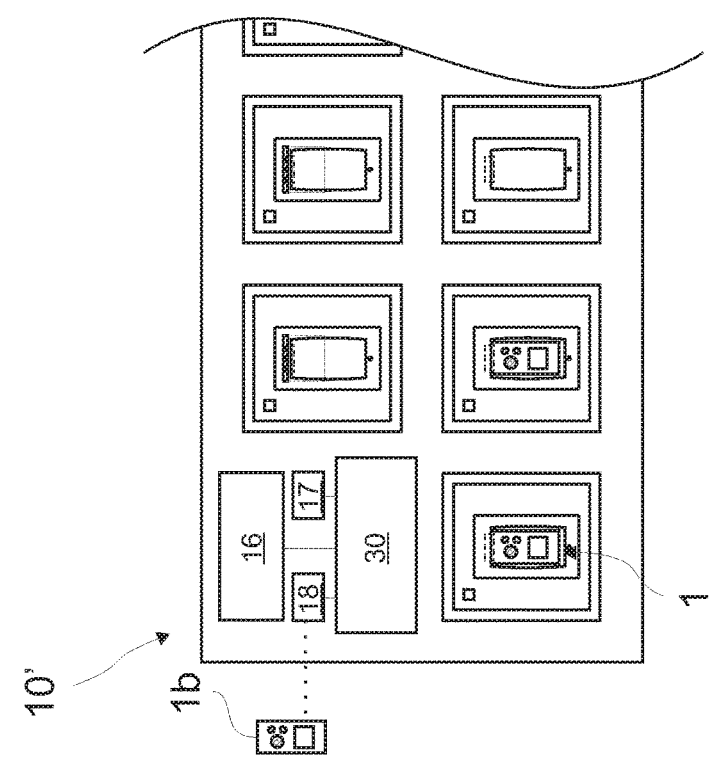
FIG. 3c is a schematic view of another state of the method according to the present invention for managing mobile devices.

The return of the return device 1b is shown in FIG. 3c and FIG. 3d. As shown in FIG. 3c, the user first scans in the return device 1b via the detection device 16, 18 during the return. As an alternative, the user does may not scan in the return device 1b, but rather may enter the return device 1b via the touchscreen. After the desire to return of the user has been detected, the storage device 10' according to the present invention fully automatically releases a suitable storage station 12 or maintenance station 14 for receiving the return device 1b. For this, the controller 30 first checks whether a maintenance station 14 is free (unoccupied). If this is the case, as shown in FIG. 3d and under the conditions described above, the maintenance station 14 and/or the corresponding storage compartment 11' is released for receiving the return device 1b. The return of the return device 1b may require an additional verification of the user by his ID card 60. As soon as the return device 1b is received in the maintenance station 14, it can be recalibrated by feeding in a test gas and provided for use again. The return device 1b is stored in the maintenance station 14 in this case.

The return device 1b can be charged and further maintained in the maintenance station 14. After the end of the maintenance, the return device 1b can be automatically transferred into a free storage station 12 and can be stored there until removal again, so that the maintenance station 14 is free for receiving another return device 1b.

While specific embodiments of the invention have been shown and described in detail to illustrate the application of the principles of the invention, it will be understood that the invention may be embodied otherwise without departing from such principles.

APPENDIX

List of Reference Numbers

1 Gas-measuring device
1a Release device
1b Return device
2 Gas inlet openings
3 Touchscreen
10; 10' Storage device
11; 11' Storage compartment
12 Storage station
13 Lamp
14 Maintenance station
15 Door handle
16, 18 Detection device
17 Warning signal release device
20 Mechanical locking device
30 Controller
40 Gas source
42 Gas feed line
50 Flap
60 ID card

What is claimed is:

1. A method for automatically managing mobile devices in a storage device with at least two storage stations, at least one maintenance station, at least one controller and at least one detection device, the method comprising the steps of:
   detecting, with the detection device, a desire to release one of the mobile devices from the storage device;
   determining, with the at least one controller, a group of mobile devices as a function of a ratio of at least one maintenance parameter of the particular mobile devices to a corresponding maintenance threshold value;
   selecting, with the at least one controller, one of the mobile devices from the group of mobile devices as a release device; and
   releasing, with the at least one controller, the selected release device, wherein the at least one maintenance parameter characterizes a particular remaining running time of the mobile devices and the corresponding maintenance threshold value corresponds with a minimally required remaining running time of the particular mobile devices and the mobile device which has the shortest remaining running time is selected as the release device.

2. A method for automatically managing mobiles devices in a storage device with at least two storage stations, at least one maintenance station, at least one controller and at least one detection device, the method comprising the steps of:

detecting, with the detection device, a desire for a return of a mobile device as a return device;

receiving of the return device into the at least one maintenance station or into one of the at least two storage stations as a function of a ratio of at least one maintenance parameter of the return device to a corresponding maintenance threshold value by means of the at least one controller, wherein the at least one maintenance parameter characterizes a remaining running time of the return device and the corresponding maintenance threshold value corresponds with a minimally required remaining running time of the return device, wherein in a case in which at least one maintenance station is free for receiving a mobile device to be maintained, the return device is received into a storage station when the return device is not one of a number of mobile devices with the shortest remaining running times and the number of mobile devices with the shortest remaining running times corresponds to a number of the at least one free maintenance station.

* * * * *